(12) United States Patent
Fishman et al.

(10) Patent No.: US 8,557,790 B2
(45) Date of Patent: Oct. 15, 2013

(54) A3 ADENOSIDE RECEPTOR AGONISTS FOR THE REDUCTION OF INTRAOCULAR PRESSURE

(75) Inventors: Pnina Fishman, Herzliya (IL); Mordechai Farbstein, Ganei Tikva (IL)

(73) Assignee: Can-Fite Biopharma Ltd., Petach Tikva (IL)

( * ) Notice: Subject to any disclaimer, the term of this patent is extended or adjusted under 35 U.S.C. 154(b) by 96 days.

(21) Appl. No.: 13/320,715

(22) PCT Filed: May 16, 2010

(86) PCT No.: PCT/IL2010/000393
§ 371 (c)(1),
(2), (4) Date: Nov. 15, 2011

(87) PCT Pub. No.: WO2010/134067
PCT Pub. Date: Nov. 25, 2010

(65) Prior Publication Data
US 2012/0065155 A1  Mar. 15, 2012

(30) Foreign Application Priority Data

May 17, 2009  (IL) .......................................... 198787

(51) Int. Cl.
*A01N 43/04* (2006.01)
*A61K 31/70* (2006.01)

(52) U.S. Cl.
USPC .................................. 514/46; 514/43; 514/45

(58) Field of Classification Search
None
See application file for complete search history.

(56) References Cited

U.S. PATENT DOCUMENTS

| | | | |
|---|---|---|---|
| 5,443,836 | A | 8/1995 | Downey et al. |
| 5,573,772 | A | 11/1996 | Downey et al. |
| 5,688,774 | A | 11/1997 | Jacobson et al. |
| 5,773,423 | A | 6/1998 | Jacobson et al. |
| 6,048,865 | A | 4/2000 | Baraldi |
| 2006/0194756 | A1 | 8/2006 | Borea et al. |

FOREIGN PATENT DOCUMENTS

| | | |
|---|---|---|
| WO | 95/02604 A1 | 1/1995 |
| WO | 97/27173 A2 | 7/1997 |
| WO | 99/06053 A1 | 2/1999 |
| WO | 99/20284 A1 | 4/1999 |
| WO | 00/59420 | 10/2000 |
| WO | 01/19360 A2 | 3/2001 |
| WO | 2007/086044 A1 | 3/2001 |
| WO | 2007/002139 | 1/2007 |

OTHER PUBLICATIONS

Avila et al. British Journal of Pharmacology (2001) vol. 134, pp. 241-245.*
Avila et al, "A1-, A2A- and A3-subtype adenosine receptors modulate intraocular pressure in the mouse", Journal, 2001, 134 241-245, Nature Publishing Group, Philadelphia, PA.
Avni et al, "Tretment of Dry Eye Syndrome with Orally Administered CF101", 2010, Opthalmology, 1287-1293, Elsevier Inc, Bethesda, Maryland.
"Can-Fite BioPharma to Initiate Phase II Clinical Trial with CF101 for the Treatment of Glaucoma", Press Release, Dec. 13, 2009, BioPharma Ltd.
C.W. Do & M.M Civan, "Swelling-activated chloride channels in aqueous humour formation: on the one side and the other", Review, Dec. 15, 2005, 187 345-352, Scandinavian Physiological Society, Philadelphia, PA.
David A.Carre et al, "Similarity of A3-adenosine and swelling-activated Cl-channels in nonpigmented ciliary epithelial cells", Journal, Nov. 17, 1999, 279 C440-C451, American Physiological Society, Philadelphia PA.
Hui Yang et al, "The Cross-Species A3 Adenosine-Receptor Antagonist MRS 1292 Inhibits Adenosine-Triggered Human Nonpigmented Ciliary Epithelial Cell Fluid Release and Reduces Mouse Intraocular Pressure". Current Eye Research, Jan. 18, 2005, 30 747-754, Taylor & Francis Group, Philadelphia PA.
Marcel Y. Avila et al, "Knockout of A3 Adenosine Receptors Reduces Mouse Intraocular Pressure" Research, Sep. 2002, 43 3021-3026, Association for Research in Vision and Ophthalmology, Philadelphia PA.
Zhao Wang et al, "Barrier qualities of the mouse eye to topically applied drugs" Research, Mar. 9, 2007, 105-112, Elsevier, Philadelphia PA.
International Preliminary Report on Patentability dated Nov. 22, 2011 for PCT/IL10/00393 filed May 16, 2010.
Written Opinion dated Nov. 2011 for PCT/IL10/00393 filed May 16, 2010.
International Search Report dated Aug. 25, 2010 for PCT/IL10/00393 filed May 16, 2010.

* cited by examiner

*Primary Examiner* — Patrick Lewis
(74) *Attorney, Agent, or Firm* — Fleit Gibbons Gutman Bongini & Bianco PL; Martin Fleit; Paul D. Bianco

(57) ABSTRACT

The present disclosure provides the use of an A3R agonist, such as IB-MECA, for reducing in a subject, preferably, human subject, intra ocular pressure (IOP). Similarly, the invention provides a pharmaceutical composition and a method for reducing IOP in a subject making use of the $A_3R$ agonist.

13 Claims, No Drawings

A3 ADENOSIDE RECEPTOR AGONISTS FOR THE REDUCTION OF INTRAOCULAR PRESSURE

FIELD OF THE INVENTION

The invention relates to compositions, methods and uses for reducing intraocular pressure (IOP) in subjects.

AND BACKGROUND OF THE INVENTION

Intraocular pressure (IOP) is an important parameter in ophthalmology. Increased IOP, or ocular hypertension, is the most important risk factor for glaucoma. Also, differences in pressure between the two eyes is often clinically significant, and potentially associated with certain types of glaucoma, as well as iritis or retinal detachment.

IOP may become elevated due to anatomical problems, inflammation of the eye, genetic factors, as a side-effect from medication, or by other factors. IOP usually increases with age and is genetically influenced. Conditions in which the IOP increases may, also at times, associated with other conditions such as dry eye syndrome.

Several publications show that A3AR may be used to regulate IOP, however, by using A3AR antagonists which were found to reduce IOP, while A3AR increase IPO [Mortimer M. Civan et al. in *Am J Physiol Cell Physiol* 279:440-451, 2000; *Current Eye Research* 30:747-754, 2005; *Investigative Ophthalmology & Visual Science* Vol. 43(9) 2002; *British Journal of Pharmacology* 134:241-245, 2001; *Acta Physiol*, 187:345-352 2006]

SUMMARY OF THE INVENTION

In accordance with the invention it was surprisingly found that administration to human subjects the $A_3$ adenosine receptor ($A_3AR$) agonist, $N^6$-(3-iodobenzyl)-adenosine-5'-N-methyluronamide (IB-MECA) resulted in lowering of intraocular pressure (IOP).

Thus, in accordance with a first aspect, the invention provides the present invention provides the use of an A3AR agonist for (i) the preparation of a pharmaceutical composition for reducing IOP in subjects with elevated IOP, particularly human subjects, or (ii) for reducing elevated IOP in subjects with IOP.

In accordance with a second aspect, the invention provides the use of A3 adenosine receptor ($A_3AR$) agonist for the preparation of a pharmaceutical composition for reducing IOP in a subject having IOP.

In accordance with a third aspect, the invention provides a pharmaceutical composition for reducing IOP in subjects, particularly human subjects, comprising, as active ingredient, an amount of $A_3AR$ agonist and a physiologically acceptable carrier, the amount of said $A_3AR$ agonist being effective to reduce IOP in a subject having IOP.

In accordance with a fourth aspect, the present invention provides a method comprising administering to a subject having IOP with an amount of $A_3AR$ agonist, the amount being effective to reduce IOP in a subject having IOP.

While the invention may be used for lowering IOP in subjects in general, it is particularly applicable for treating subjects with elevated IOP in order to reduce the IOP to lower levels, preferably to statistically significant lower levels.

DETAILED DESCRIPTION OF EXEMPLARY EMBODIMENTS

The present invention provides, by one embodiment, a method comprising providing a subject, e.g. being diagnosed with elevated IOP, with an amount of $A_3$ adenosine receptor ($A_3AR$) agonist, which is effective to reduce the IOP to a level that is at least statistically significant lower than the level before treatment, and preferably to a level that is considered to represent normal ocular pressure.

As appreciated, while the invention is described in the following detailed description with reference to the above method, it is to be understood that also encompassed within the present invention are compositions comprising the $A_3AR$ agonist for use in said treatment; as well as uses, as defined hereinabove and below.

In the context of the present invention the term "elevated IOP" denotes an IOP which is above what is clinically considered as normal IOP level in healthy subjects. As may be appreciated, the normal IOP and hence what may be considered as elevated may vary depending on a variety of demographic and other factors. For example, seeing that IOP is to some extent age dependent, what is considered normal and hence what may be regarded as elevated IOP may also be age-dependent. Furthermore the definition of normal IOP and hence of elevated IOP may be dependent on genetic, demographic and a variety of other factors.

Conditions of elevated TOP include, but are not limited to, glaucoma, inflammatory eye conditions that result in elevated TOP, conditions with increased TOP due to anatomical problems, increased TOP that results from a side effect of other medications, and others. The terms "treating" or "treatment", and the like are used herein to refer to obtaining a desired pharmacological and physiological effect. The effect may be prophylactic in terms of preventing or partially preventing an increased in the IOP level, and/or may be therapeutic in terms of reduction in the IOP level. The term "treatment", as used herein, covers any treatment of a disease in a mammal, particularly a human, and includes: (a) preventing IOP elevation from occurring in an individual which may be predisposed to IOP elevation although not having yet been diagnosed as having it; or (b) lowering the IOP level in subjects, in some embodiments, being diagnosed with elevated IOP.

In some embodiments, the treatment refers to treatment of IOP in subjects being diagnosed for having Keratoconjunctivitis Sicca (KCS) also known as the dry eye syndrome.

The term "$A_3$ adenosine receptor agonist" ($A_3AR$ agonist) in the context of the present invention refers to any molecule capable of specifically binding to the $A_3AR$, thereby fully or partially activating said receptor. The $A_3AR$ agonist is thus a molecule that exerts its prime effect through the binding and activation of the $A_3AR$. This means that at the doses it is being administered it essentially binds to and activates only the $A_3AR$. In a preferred embodiment, an $A_3AR$ agonist has a binding affinity ($K_i$) to the human $A_3AR$ in the range of less than 100 nM, typically less than 50 nM, preferably less than 20 nM, more preferably less than 10 nM and ideally less than 5 nM. Particularly preferred are $A_3AR$ agonists that have a $K_i$ to the human $A_3R$ of less than 2 nM and desirably less than 1 nM.

It should be noted that some $A_3AR$ agonists can also interact with and activate other receptors with lower affinities (namely a higher Ki). A molecule will be considered an $A_3AR$ agonist in the context of the invention (namely a molecule that exerts its prime effect through the binding and activation $A_3AR$) if its affinity to the $A_3AR$ is at least 3 times (i.e. its Ki to the $A_3AR$ is at least 3 times lower), preferably 10 times, desirably 20 times and most preferably at least 50 times larger than the affinity to any other of the adenosine receptors (i.e. $A_1$, $A_{2a}$ and $A_{2b}$).

The affinity of an $A_3AR$ agonist to the human $A_3AR$ as well as its relative affinity to the other human adenosine receptors can be determined by a number of assays, such as a binding assay. Examples of binding assays include providing membranes containing a receptor and measuring the ability of the $A_3AR$ agonist to displace a bound radioactive agonist; utilizing cells that display the respective human adenosine receptor and measuring, in a functional assay, the ability of the $A_3AR$ agonist to activate or deactivate, as the case may be, downstream signaling events such as the effect on adenylate cyclase measured through increase or decrease of the cAMP level; etc. Clearly, if the administered level of an $A_3AR$ agonist is increased such that its blood level reaches a level approaching that of the Ki of the $A_1$, $A_{2a}$ and $A_{2b}$ adenosine receptors, activation of these receptors may occur following such administration, in addition to activation of the $A_3AR$. An $A_3AR$ agonist is thus preferably administered at a dose such that the blood level is such so that essentially only the $A_3AR$ will be activated.

According to an embodiment of the invention, the $A_3AR$ agonist is a compound that exerts its prime effect through the binding and activation of the adenosine $A_3AR$.

Some $A_3AR$ agonists are purine derivatives falling within the scope of the general formula (I):

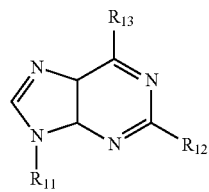

(I)

wherein, $R_{11}$ represents an alkyl, hydroxyalkyl, carboxyalkyl or cyanoalkyl or a group of the following general formula (II):

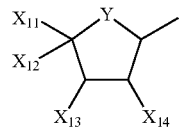

(II)

in which:

Y represents oxygen, sulfur or $CH_2$;

$X_{11}$ represents H, alkyl, $R^eR^fNC(=O)$— or $HOR^g$—, wherein $R^e$ and $R^f$ may be the same or different and are selected from the group consisting of hydrogen, alkyl, amino, haloalkyl, aminoalkyl, BOC-aminoalkyl, and cycloalkyl or are joined together to form a heterocyclic ring containing two to five carbon atoms; and $R^g$ is selected from the group consisting of alkyl, amino, haloalkyl, aminoalkyl, BOC-aminoalkyl, and cycloalkyl;

$X_{12}$ is H, hydroxyl, alkylamino, alkylamido or hydroxyalkyl;

$X_{13}$ and $X_{14}$ represent independently hydrogen, hydroxyl, amino, amido, azido, halo, alkyl, alkoxy, carboxy, nitrilo, nitro, trifluoro, aryl, alkaryl, thio, thioester, thioether, —OCOPh, —OC(=S)OPh or both $X_{13}$ and $X_{14}$ are oxygen connected to >C=S to form a 5-membered ring, or $X_{12}$ and $X_{13}$ form the ring of formula (III):

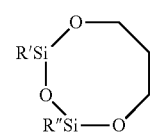

(III)

where R' and R" represent independently an alkyl group;

$R_{12}$ is selected from the group consisting of hydrogen, halo, alkylether, amino, hydrazido, alkylamino, alkoxy, thioalkoxy, pyridylthio, alkenyl; alkynyl, thio, and alkylthio; and $R_{13}$ is a group of the formula —$NR_{15}R_{16}$ wherein $R_{15}$ is a hydrogen atom or a group selected from alkyl, substituted alkyl or aryl-NH—C(Z)—, with Z being O, S, or $NR^a$ with $R^e$ having the above meanings; wherein when $R_{15}$ is hydrogen than —$R_{16}$ is selected from the group consisting of R- and S-1-phenylethyl, benzyl, phenylethyl or anilide groups unsubstituted or substituted in one or more positions with a substituent selected from the group consisting of alkyl, amino, halo, haloalkyl, nitro, hydroxyl, acetamido, alkoxy, and sulfonic acid or a salt thereof; benzodioxanemethyl, furfuryl, L-propylalanyl-aminobenzyl, β-alanylamino-benzyl, T-BOC-β-alanylaminobenzyl, phenylamino, carbamoyl, phenoxy or cycloalkyl; or $R_{16}$ is a group of the following formula (IV):

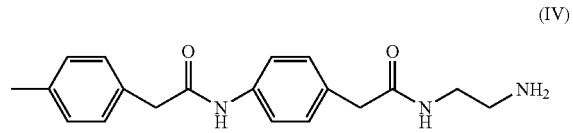 [SMILES: Cc1ccc(CC(=O)Nc2ccc(CC(=O)NCCN)cc2)cc1]

(IV)

or when $R_{15}$ is an alkyl or aryl-NH—C(Z)—, then, $R_{16}$ is selected from the group consisting of heteroaryl-$NR^a$—C(Z)—, heteroaryl-C(Z)—, alkaryl-$NR^a$—C(Z)—, alkaryl-C(Z)—, aryl-NR—C(Z)— and aryl-C(Z)—; Z representing an oxygen, sulfur or amine; or a physiologically acceptable salt of the above compound.

The characteristic of some adenosine $A_3AR$ agonists and methods of their preparation are described in detail in, inter alia, U.S. Pat. No. 5,688,774; U.S. Pat. No. 5,773,423, U.S. Pat. No. 5,573,772, U.S. Pat. No. 5,443,836, U.S. Pat. No. 6,048,865, WO 95/02604, WO 99/20284, WO 99/06053, WO 97/27173 and WO 01/19360, all of which are incorporated herein by reference.

Exemplary $A_3AR$ agonist (disclosed in U.S. Pat. No. 5,688, 774 at column 4, lines 67-column 6, line 16; column 5, lines 40-45; column 6, lines 21-42; column 7, lines 1-11; column 7, lines 34-36; and column 7, lines 60-61):

$N^6$-(3-iodobenzyl)-9-methyladenine;
$N^6$-(3-iodobenzyl)-9-hydroxymethyladenine;
R—$N^6$-(3-iodobenzyl)-9-(2,3-dihydroxypropyl)adenine;
S—$N^6$-(3-iodobenzyl)-9-(2,3-dihydroxypropyl)adenine;
$N^6$-(3-iodobenzyladenin-9-yl)acetic acid;
$N^6$-(3-iodobenzyl)-9-(3-cyanopropyl)adenine;
2-chloro-$N^6$-(3-iodobenzyl)-9-methyladenine;
2-amino-$N^6$-(3-iodobenzyl)-9-methyladenine;
2-hydrazido-$N^6$-(3-iodobenzyl)-9-methyladenine;
$N^6$-(3-iodobenzyl)-2-methylamino-9-methyladenine;
2-dimethylamino-$N^6$-(3-iodobenzyl)-9-methyladenine;
$N^6$-(3-iodobenzyl)-9-methyl-2-propylaminoadenine;
2-hexylamino-$N^6$-(3-iodobenzyl)-9-methyladenine;

N⁶-(3-iodobenzyl)-2-methoxy-9-methyladenine;

N⁶-(3-iodobenzyl)-9-methyl-2-methylthioadenine;

N⁶-(3-iodobenzyl)-9-methyl-2-(4-pyridylthio)adenine;

(1S,2R,3S,4R)-4-(6-amino-2-phenylethylamino-9H-purin-9-yl)cyclopentane-1,2,3-triol;

(1S,2R,3S,4R)-4-(6-amino-2-chloro-9H-purin-9-yl)cyclopentane-1,2,3-triol;

(±)-9-[2α,3α-dihydroxy-4β-(N-methylcarbamoyl)cyclopent-1β-yl)]-N⁶-(3-iodobenzyl)-adenine;

2-chloro-9-(2'-amino-2',3'-dideoxy-β-D-5'-methyl-arabinofuronamido)-N⁶-(3-iodobenzyl)adenine;

2-chloro-9-(2',3'-dideoxy-2'-fluoro-β-D-5'-methyl-arabino furonamido)-N⁶-(3-iodobenzyl)adenine;

9-(2-acetyl-3-deoxy-β-D-5-methyl-ribofuronamido)-2-chloro-N⁶(3-iodobenzyl)adenine;

2-chloro-9-(3-deoxy-2-methanesulfonyl-β-D-5-methyl-ribofuronamido)-N⁶-(3-iodobenzyl)adenine;

2-chloro-9-(3-deoxy-β-D-5-methyl-ribofuronamido)-N⁶-(3-iodobenzyl)adenine;

2-chloro-9-(3,5-1,1,3,3-tetraisopropyldisiloxyl-β-D-5-ribofuranosyl)-N⁶-(3-iodobenzyl)adenine;

2-chloro-9-(2',3'-O-thiocarbonyl-β-D-5-methyl-ribofuronamido)-N⁶-(3-iodobenzyl)adenine;

9-(2-phenoxythiocarbonyl-3-deoxy-β-D-5-methyl-ribofuronamido)-2-chloro-N⁶-(3-iodobenzyl)adenine;

1-(6-benzylamino-9H-purin-9-yl)-1-deoxy-N,4-dimethyl-β-D-ribofuranosiduronamide;

2-chloro-9-(2,3-dideoxy-β-D-5-methyl-ribofuronamido)-N⁶ benzyladenine;

2-chloro-9-(2'-azido-2',3'-dideoxy-β-D-5'-methyl-arabinofuronamido)-N⁶-benzyladenine;

2-chloro-9-(β-D-erythrofuranoside)-N⁶-(3-iodobenzyl)adenine;

N⁶-(benzodioxanemethyl)adenosine;

1-(6-furfurylamino-9H-purin-9-yl)-1-deoxy-N-methyl-β-D-ribofuranosiduronamide;

N⁶-[3-(L-prolylamino)benzyl]adenosine-5'-N-methyluronamide;

N⁶-[3-(β-alanylamino)benzyl]adenosine-5'-N-methyluronamide;

N⁶-[3-(N-T-Boc-β-alanylamino)benzyl]adenosine-5'-N-methyluronamide 6-(N'-phenylhydrazinyl)purine-9-β-ribofuranoside-5'-N-methyluronamide;

6-(O-phenylhydroxylamine)purine-9-β-ribofuranoside-5'-N-methyluronamide;

9-(β-D-2',3'-dideoxyerythrofuranosyl)-N⁶-[(3-β-alanylamino)benzyl]adenosine;

9-(β-D-erythrofuranoside)-2-methylamino-N⁶-(3-iodobenzyl)adenine;

2-chloro-N-(3-iodobenzyl)-9-(2-tetrahydrofuryl)-9H-purin-6-amine;

2-chloro-(2'-deoxy-6'-thio-L-arabinosyl)adenine; and 2-chloro-(6'-thio-L-arabinosyl)adenine.

Other exemplary A₃AR agonists, disclosed in U.S. Pat. No. 5,773,423, are compounds of the formula (V):

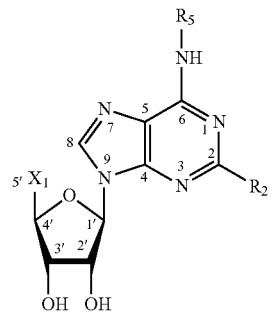

wherein $X_1$ is $R^aR^bNC(=O)$, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;

$R_2$ is selected from the group consisting of hydrogen, halo, $C_1$-$C_{10}$ alkoxy, amino, $C_2$-$C_{10}$ alkenyl, and $C_2$-$C_{10}$ alkynyl; and $R_5$ is selected from the group consisting of R- and S-1-phenylethyl, an unsubstituted benzyl group, and a benzyl group substituted in one or more positions with a substituent selected from the group consisting of $C_1$-$C_{10}$ alkyl, amino, halo, $C_1$-$C_{10}$ haloalkyl, nitro, hydroxy, acetamido, $C_1$-$C_{10}$ alkoxy, and sulfo.

More specific compounds include those of the above formula wherein $R^a$ and $R^b$ may be the same or different and are selected from the group consisting of hydrogen and $C_1$-$C_{10}$ alkyl, particularly when $R_2$ is hydrogen or halo, especially hydrogen.

Additional specific compounds are those compounds wherein $R^a$ is hydrogen and $R_2$ is hydrogen, particularly when $R_5$ is unsubstituted benzyl.

More specific compounds are such compounds wherein $R^b$ is a $C_1$-$C_{10}$ alkyl or $C_3$-$C_{10}$ cycloalkyl, particularly a $C_1$-$C_{10}$ alkyl, and more particularly methyl.

Especially specific are those compounds where $R^a$ is hydrogen, $R^b$ is $C_1$-$C_{10}$ alkyl or $C_3$-$C_{10}$ cycloalkyl, and $R_5$ is R- or S-1-phenylethyl or a benzyl substituted in one or more positions with a substituent selected from the group consisting of halo, amino, acetamido, $C_1$-$C_{10}$ haloalkyl, and sulfo, where the sulfo derivative is a salt, such as a triethylammonium salt.

An example of an especially preferred compound out of those disclosed in U.S. Pat. No. 5,773,423 is IB-MECA. In addition, those compounds in which $R_2$ is a $C_2$-$C_{10}$ alkenylene of the formula $R^d$—C=C— where $R^d$ is a $C_1$-$C_8$ alkyl are particularly noted in this publication. Also specific are those compounds wherein $R_2$ is other than hydrogen, particularly those wherein $R_2$ is halo, $C_1$-$C_{10}$ alkylamino, or $C_1$-$C_{10}$ alkylthio, and, more preferably, when additionally $R^a$ is hydrogen, $R^b$ is a $C_1$-$C_{10}$ alkyl, and/or $R_5$ is a substituted benzyl.

Such specifically disclosed compounds include 2-chloro-N⁶-(3-iodobenzyl)-9-[5-(methylamido)-β-D-ribofuranosyl]-adenine, N⁶-(3-iodobenzyl)-2-methylamino-9-[5-(methylamido)-β-D-ribofuranosyl]-adenine, and N⁶-(3-iodobenzyl)-2-methylthio-9-[5-(methylamido)-β-D-ribofuranosyl]-adenine.

Further exemplary A₃AR agonists disclosed in U.S. Pat. No. 5,773,423 are modified xanthine-7-ribosides having the formula (VI):

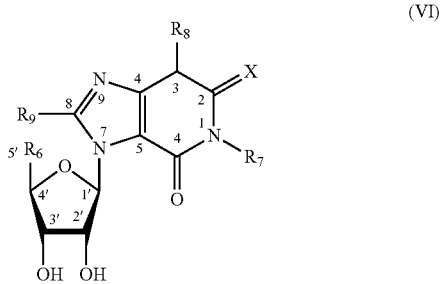

(VI)

wherein

X is O;

$R_6$ is $R^aR^bNC(=O)$, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;

$R_7$ and $R_8$ may be the same or different and are selected from the group consisting of $C_1$-$C_{10}$ alkyl, R- and S-1-phenylethyl, an unsubstituted benzyl group, and a benzyl group substituted in one or more positions with a substituent selected from the group consisting of $C_1$-$C_{10}$ alkyl, amino, halo, $C_1$-$C_{10}$ haloalkyl, nitro, hydroxy, acetamido, $C_1$-$C_{10}$ alkoxy, and sulfo; and $R_9$ is selected from the group consisting of halo, benzyl, phenyl, and $C_3$-$C_{10}$ cycloalkyl.

WO 99/06053 discloses in examples 19-33 compounds selected from:

$N^6$-(4-biphenyl-carbonylamino)-adenosine-5'-N-ethyluronamide;

$N^6$-(2,4-dichlorobenzyl-carbonylamino)-adenosine-5'-N-ethyluronamide;

$N^6$-(4-methoxyphenyl-carbonylamino)-adenosine-5'-N-ethyluronamide;

$N^6$-(4-chlorophenyl-carbonylamino)-adenosine-5'-N-ethyluronamide;

$N^6$-(phenyl-carbonylamino)-adenosine-5'-N-ethyluronamide;

$N^6$-(benzylcarbamoylamino)-adenosine-5'-N-ethyluronamide;

$N^6$-(4-sulfonamido-phenylcarbamoyl)-adenosine-5'-N-ethyluronamide;

$N^6$-(4-acetyl-phenylcarbamoyl)-adenosine-5'-N-ethyluronamide;

$N^6$—((R)-α-phenylethylcarbamoyl)-adenosine-5'-N-ethyluronamide;

$N^6$—((S)-α-phenylethylcarbamoyl)-adenosine-5'-N-ethyluronamide;

$N^6$-(5-methyl-isoxazol-3-yl-carbamoyl)-adenosine-5'-N-ethyluronamide;

$N^6$-(1,3,4-thiadiazol-2-yl-carbamoyl)-adenosine-5'-N-ethyluronamide;

$N^6$-(4-n-propoxy-phenylcarbamoyl)-adenosine-5'-N-ethyluronamide;

$N^6$-bis-(4-nitrophenylcarbamoyl)-adenosine-5'-N-ethyluronamide; and $N^6$-bis-(5-chloro-pyridin-2-yl-carbamoyl)-adenosine-5'-N-ethyluronamide.

Specific examples of $A_3AR$ agonist which may be employed according to general formula (I to III) include, without being limited thereto, $N^6$-2-(4-aminophenyl)ethyladenosine (APNEA), $N^6$-(4-amino-3-iodobenzyl)adenosine-5'-(N-methyluronamide) (AB-MECA), $N^6$-(3-iodobenzyl)-adenosine-5'-N-methyluronamide (IB-MECA) and 2-chloro-$N^6$-(3-iodobenzyl)-adenosine-5'-N-methyluronamide (Cl-IB-MECA). IB-MECA is the most preferred compound in accordance with the invention.

According to another embodiment, the $A_3AR$ agonist may be an oxide derivative of adenosine, such as $N^6$-benzyladenosine-5'-N-alkyluronamide-$N^1$-oxide or $N^6$-benzyladenosine-5'-N-dialkyluronamide-$N^1$-oxide, wherein the 2-purine position may be substituted with an alkoxy, amino, alkenyl, alkynyl or halogen.

The non-cyclic carbohydrate groups (e.g. alkyl, alkenyl, alkynyl, alkoxy, aralkyl, alkaryl, alkylamine, etc) forming part of the substituent of the compounds of formulae (I), (II) or (III) are either branched or unbranched, preferably containing from one or two to twelve carbon atoms.

When referring to "physiologically acceptable salts" of the compounds employed by the present invention it is meant any non-toxic alkali metal, alkaline earth metal, and ammonium salt commonly used in the pharmaceutical industry, including the sodium, potassium, lithium, calcium, magnesium, barium ammonium and protamine zinc salts, which are prepared by methods known in the art. The term also includes non-toxic acid addition salts, which are generally prepared by reacting the compounds of this invention with a suitable organic or inorganic acid. The acid addition salts are those which retain the biological effectiveness and qualitative properties of the free bases and which are not toxic or otherwise undesirable. Examples include, inter alia, acids derived from mineral acids, hydrochloric, hydrobromic, sulfuric, nitric, phosphoric, metaphosphoric and the like. Organic acids include, inter alia, tartaric, acetic, propionic, citric, malic, malonic, lactic, fumaric, benzoic, cinnamic, mandelic, glycolic, gluconic, pyruvic, succinic salicylic and arylsulphonic, e.g. p-toluenesulphonic, acids.

The terms "effective amount" or "amount effective to" in the context of the present invention refer to an amount of $A_3AR$ agonist which prevents elevation of IOP or reduces IOP levels (a statistically significant reduction), particularly reduction in elevated IP, in patients. The "effective amount" can be readily determined, in accordance with the invention, by administering to a plurality of tested subjects various amounts of the $A_3AR$ agonist and then plotting the physiological response (for example an integrated "SS index" combining several of the therapeutically beneficial effects) as a function of the amount. Alternatively, the effective amount may also be determined, at times, through experiments performed in appropriate animal models and then extrapolating to human beings using one of a plurality of conversion methods; or by measuring the plasma concentration or the area under the curve (AUC) of the plasma concentration over time and calculating the effective dose so as to yield a comparable plasma concentration or AUC. As known, the effective amount may depend on a variety of factors such as mode of administration (for example, oral administration may require a higher dose to achieve a given plasma level or AUC than an intravenous administration); the age, weight, body surface area, gender, health condition and genetic factors of the subject; other administered drugs; etc.

In the following, unless otherwise indicated, dosages are indicated in weight/Kg, meaning weight of administered $A_3AR$ agonist (e.g. IB-MECA) per kilogram of body weight of the treated subject in each administration. For example, mg/Kg and microgram/Kg denote, respectively, milligrams of administered agent and micrograms of administered agent per kilogram of body weight of the treated subject.

The effective amount is preferably less than about 1 mg/kg body weight, particularly less than about 500 µg/kg or even less than about 200 µg/kg body weight or at times less than about 100 µg/kg body weight or even less than about less than 50 µg/kg body weight. With respect to IB-MECA, the effective amount is preferably less than 5 mg each dose, for once daily administration (namely a dose less than about 70 µg/kg body weight, assuming an average individual weight of about 70 kg), and less than about 4 mg each dose (i.e. less than about 57 µg/kg body weight), for twice daily administration. The dose of IB-MECA is more preferably less than about 2 mg each dose and typically between about 0.1-1 mg each dose, for either once or twice daily administration (the corresponding dosages in weight per body weight being about 29 µg/kg and about 1.5-15 µg/kg body weight, respectively). With respect to Cl-IB-MECA, the effective amount is preferably less than 40 mg each dose, for once or twice daily administration (namely a dose less than about 570 µg/kg body weight, assuming an average individual weight of about 70 kg). The dose of Cl-IB-MECA is more preferably less than about 30 or less than about 20 mg each dose, for either once or twice daily administration (the corresponding dosages in weight per body weight being about 430 µg/kg and about 285 µg/kg body weight, respectively).

The administration of the $A_3AR$ agonist to an individual may be together with a pharmaceutically acceptable carrier. In the case where the administration is oral, the carrier is one that is acceptable for oral administration. In the case where the administration is topical, the carrier is one that is acceptable for topical administration, one example being ocular administration.

By the term "pharmaceutically acceptable carrier" it is meant any one of inert, non-toxic materials, which do not react with the $A_3AR$ agonist and which can be added to formulations as diluents or carriers or to give form or consistency to the formulation.

An oral formulation may be in the form of a pill, capsule, in the form of a syrup, an aromatic powder, and other various forms. The carrier is selected at times based on the desired form of the formulation. The carrier may also, at times, have the effect of improving the delivery or penetration of the active ingredient to the target tissue, for improving the stability of the active ingredient, for slowing clearance rates of the active ingredient, for imparting slow release properties of the active ingredient, for reducing undesired side effects etc. The carrier may also be a substance that stabilizes the formulation (e.g. a preservative), for providing the formulation with an edible flavor, etc. The carriers may be any of those conventionally used and is limited only by chemical-physical considerations, such as solubility and lack of reactivity with the $A_3AR$ agonist, and by the route of administration. The carrier may include additives, colorants, diluents, buffering agents, disintegrating agents, moistening agents, preservatives, flavoring agents, and pharmacologically compatible carriers. In addition, the carrier may be an adjuvant, which, by definition are substances affecting the action of the active ingredient in a predictable way.

Typical examples of carriers suitable for oral administration comprise (a) liquid solutions, where an effective amount of the active substance is dissolved in diluents, such as water, saline, natural juices, alcohols, syrups, etc.; (b) capsules (e.g. the ordinary hard- or soft-shelled gelatin type containing, for example, surfactants, lubricants, and inert fillers), tablets, lozenges (wherein the active substance is in a flavor, such as sucrose and acacia or tragacanth or the active substance is in an inert base, such as gelatin and glycerin), and troches, each containing a predetermined amount of the tragacanth as solids or granules; (c) powders; (d) suspensions in an appropriate liquid; (e) suitable emulsions; (f) liposome formulation; and others.

A topical formulation may be in any form suitable for topical administration, including, without being limited thereto, an ophthalmic solution (e.g. eye drops), an ophthalmic gel or an ophthalmic ointment or oily lotion. Topical administration of the $A_3AR$ agonist also comprises the use of ophthalmic patches carrying the $A_3AR$ agonist in a suitable drug containing layer and to be placed on top of the eyelid as well as to Ocular inserts which are devices containing the $A_3AR$ agonist and placed into the inferior or superior conjunctival sacs (see for example WO00/59420).

Eye drops may be prepared by dissolving $A_3AR$ agonist in a sterile aqueous solution such as saline, buffering solution etc., or by combining powder compositions to be dissolved before use. Other additives may be included in the eye drops such as isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, etc.).

Eye ointments may be prepared by mixing A3AR agonist into a base. Examples of the base for eye ointment include petrolatum, selen 50, Plastibase, macrogol, etc., but not limited thereto.

Some exemplary ophthalmic viscosity enhancers that can be used in the present formulation include: carboxymethyl cellulose sodium; methylcellulose; hydroxypropyl cellulose; hydroxypropylmethyl cellulose; hydroxyethyl cellulose; polyethylene glycol 300; polyethylene glycol 400; polyvinyl alcohol; and povidone.

Some natural products, such as veegum, alginates, xanthan gum, gelatin, acacia and tragacanth, may also be used to increase the viscosity of ophthalmic solutions.

A tonicity is important because hypotonic eye drops cause an edema of the cornea, and hypertonic eye drops cause deformation of the cornea. The ideal tonicity is approximately 300 mOsM. The tonicity can be achieved by methods described in Remington: The Science and Practice of Pharmacy, known to those versed in the art.

The invention also provides a package (kit) comprising one or more $A_3R$ agonists and instructions for use of the A3R agonist, the instructions being in line with the herein disclosed method of the invention.

As used herein, the forms "a", "an" and "the" include singular as well as plural references unless the context clearly dictates otherwise. For example, the term "an $A_3AR$ agonist" includes one or more compounds which are capable of specifically binding to the $A_3AR$, thereby fully or partially activating said receptor.

Further, as used herein, the term "comprising" is intended to mean that the composition include the recited active agent, i.e. $A_3AR$ agonist, but not excluding other elements, such as physiologically acceptable carriers and excipients as well as other active agents. The term "consisting essentially of" is used to define compositions which include the recited elements but exclude other elements that may have an essential significance on reducing IOP. "Consisting of" shall thus mean excluding more than trace elements of other elements. Embodiments defined by each of these transition terms are within the scope of this invention.

Further, all numerical values, e.g. when referring the amounts or ranges of the elements constituting the composition comprising the $A_3AR$ agonist as an active ingredient, are approximations which are varied (+) or (−) by up to 20%, at times by up to 10% of from the stated values. It is to be understood, even if not always explicitly stated that all numerical designations are preceded by the term "about".

The invention will now be exemplified in the following description of experiments that were carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow.

Non-Limiting Examples

A clinical study was conducted in patients with dry eye symptoms. The patients received an oral administration of IB-MECA at a dose of 1 mg or placebo, twice daily. Surprisingly, in addition to amelioration of some of the dry eye symptoms, the study showed an effect of IB-MECA in decreasing IOP in the tested subjects, in general, and in patients with elevated IOP, in particular.

Active Ingredient and Formulation

The $A_3AR$ agonist that was used was a clinical grade of the compound known generically as 1-Deoxy-1-[6-[[(3-iodophenyl)methyl]amino]-9H-purine-9-yl]-N-methyl-D-ribofuranuronamide or as $N^6$-(3-iodobenzyl)-adenosine-5'-N-methyluronamide (IB-MECA), that was synthesized for Can-Fite BioPharma, under good clinical practice (GMP) by Albany Molecular Research Inc, Albany, N.Y., USA.

In a first phase of the study, IB-MECA was formulated initially in oval softgel capsules ("IB-MECA capsules"). Each of the capsules contained solutions of IB-MECA in Cremophor RH 40 and Miglyol 812 with the composition shown in the following Table 1:

TABLE 1

| IB-MECA capsules | | |
|---|---|---|
| Ingredient | Capsule | % W/W |
| IB-MECA | 1.05 mg | 0.210 |
| Polyoxyl 45 Castor Oil, USP (Cremophor RH 40) | 325.975 mg | 65.195 |
| Miglyol 812 | 172.975 mg | 34.595 |

In the second phase of the study IB-MECA was formulated in the form of tablets ("IB-MECA tablets") that included, each, the ingredients, as shown in the following Table 2:

TABLE 2

| IB-MECA Tablets | | |
|---|---|---|
| | Ingredient | Amount (mg) |
| Intragranular | IB-MECA | 1.000 |
| | Pregelatinized Starch | 10.00 |
| | Croscarmellose Sodium | 2.000 |
| | Lactose Monohydrate 310 | 64.25 |
| | Microcrystalline Cellulose | 20.00 |
| Extragranular | Croscarmellose Sodium | 2.000 |
| | Magnesium Stearate | 0.7500 |
| | Total | 100.00 |
| Coating | Opadry White | 3.000 |
| | Total | 103.0 |

Methods:

(a) Study Design

This study was a Phase 2, randomized, double-masked, placebo-controlled, parallel-group study in adult males and females, aged 18 years and over, with a diagnosis of moderate-to-severe Keratoconjunctivitis Sicca (KCS). Patients were randomized to receive either IB-MECA 1 mg or matching placebo, given orally, twice daily, for 12 weeks. A Screening Period of up to 4 weeks that includes a 2-week run-in period preceded a 12-week treatment period, followed by a 2-week follow-up period.

Some patients received either the IB-MECA capsules or a matching placebo and others received the IB-MECA tablets or a matching placebo. The breakdown in the number of patients for each of the administered formulation is shown in the following Table 3:

TABLE 3

| Treatment groups | | |
|---|---|---|
| Type | Treatment | No.* |
| Capsule | IB-MECA | 11 |
| | Placebo | 14 |
| Tablets | IB-MECA | 24 |
| | Placebo | 22 |

*No. of evaluable patients (b) Patients' Inclusion Criteria

Eligible patients to be included in the study were adult males or females, aged 18 years and over, with a diagnosis of moderate-to-severe KCS as defined by:

(1) at least 1 of the following ocular symptoms scored at ≥2, where 0=none and 4=very severe/interferes with normal activities: photophobia, blurred vision, foreign body sensation, soreness or pain, itching, burning, dryness; AND (2) ST (without anesthesia)<7 mm/5 min in either eye; AND (3) Positive FS, defined as a corneal punctuate fluorescein staining score of ≥1 in either eye, where 0=none and 3=severe. Use of topical ocular treatments was banned during the course of the study other than unreserved artificial tears (REFRESH) up to 8 times/day for the duration of the trial. Also banned was periocular cosmetic application.

(c) Patients' Exclusion Criteria

Patients were excluded from the study if they had Sjögren's Syndrome with significant systemic non-exocrine gland involvement, Stevens-Johnson Syndrome, post-burn ocular injury, or chronic ocular disease other than KCS requiring topical treatment. Excluded were also patients being administered topical cyclosporine eye drops or systemic cyclosporine within 3 months prior to the Screening Visit; disease-modifying drugs, including methotrexate and biological agents, whose dose has been changed within 3 months prior to the Screening Visit or was expected to change during the trial; oral corticosteroids>10 mg prednisone, or equivalent, per day; or topical steroids within 2 weeks prior to the Screening Visit and for the duration of the study. Additional exclusion criteria included ocular herpes simplex virus infection; use of contact lenses concomitantly or within 3 months; persistent intraocular inflammation or infection; active blepharitis of greater than mild degree; recent surgical occlusion of the lacrimal puncta; subepithelial corneal scarring; anesthetic or neurotrophic corneas; presence or history of uncontrolled asthma, uncontrolled arterial hypertension or symptomatic hypotension; significant cardiac arrhythmia or conduction block, congestive heart failure, or any other evidence of clinically significant heart disease; other clinically significant findings on screening electrocardiogram (ECG); hemoglobin level<9.0 gm/L; platelet count<125,000/mm$^3$; white blood cell (WBC) count<3500/mm$^3$; serum creatinine level outside the laboratory's normal limits; liver aminotransferase levels greater than 2 times the laboratory's upper limit of normal; known or suspected immunodeficiency or human immunodeficiency virus positively; pregnancy, planned pregnancy, lactation, or inadequate contraception as judged by the Investigator; history of drug or alcohol dependence; history of serious drug or iodine allergy or sensitivity; previous receipt of CF101; history of malignancy within the past 5 years (excluding basal cell carcinoma of the skin); significant acute or chronic medical, ophthalmic, or psychiatric illness that, in the judgment of the Investigator, could compromise patient safety, limit the patient's ability to complete the study, and/or compromise the objectives of the study; participation in another investigational drug or vaccine trial concurrently or within 30 days; or other conditions which would confound the study evaluations or endanger the safety of the patient.

(d) Study Endpoints

The study endpoints were measures relating to KCS. However, other parameters were measured including IOP.

Results

The IOP was measured in the patients (those receiving tables as well as from those receiving the capsules) prior to first treatment ("baseline") and at the end of the 12 weeks treatment period ("week 12"). The results are shown in the following Table 4:

TABLE 4

IB-MECA effectiveness

| Treatment group | IOP | N | Mean | Standard error |
|---|---|---|---|---|
| IB-MECA | at baseline | 35 | 14.14 | 0.57 |
|  | week 12 | 35 | 13.00 | 0.52 |
|  | change | 35 | −1.14 | 0.56 |
|  | % change | 35 | −6.07 | 3.38 |
| Placebo | at baseline | 36 | 14.42 | 0.47 |
|  | week 12 | 36 | 13.81 | 0.38 |
|  | change | 36 | −0.61 | 0.43 |
|  | % change | 36 | −1.95 | 3.03 |

As can be seen, the IB-MECA treated group demonstrated a much more pronounce decrease in IOP than the placebo group (a decrease of 6.07% change versus 1.95% in the placebo group; p<0.05). This led to the conclusion that IB-MECA as well as other A$_3$AR agonists are potential drugs for reducing IOP.

The invention claimed is:

1. A method for reducing intraocular pressure (IOP) in a subject comprising administrating to the subject an amount of A$_3$ adenosine receptor (A$_3$AR) agonist, the amount being effective to reduce IOP.

2. The method of claim 1, wherein the subject is a human subject.

3. The method of claim 1, wherein the subject has elevated IOP.

4. The method of claim 1, comprising oral administration of the A$_3$AR agonist.

5. The method of claim 1, wherein the A$_3$AR agonist is administered twice a day to said subject.

6. The method of claim 5, wherein the A$_3$AR agonist is administered twice a day to said subject.

7. The method of claim 1, comprising topical administration of the A$_3$AR agonist.

8. The method of claim 1, wherein said A$_3$AR agonist is administered to the eye.

9. The method of claim 1, wherein the A$_3$AR agonist is selected from the group consisting of N$^6$-2-(4-aminophenyl)ethyladenosine (APNEA), N$^6$-(4-amino-3-iodobenzyl)adenosine-5'-(N-methyluronamide) (AB-MECA), N$^6$-(3-iodobenzyl)-adenosine-5'-N-methyluronamide (IB-MECA) and 2-chloro-N$^6$-(3-iodobenzyl)-adenosine-5'-N-methyluronamide (Cl-IB-MECA).

10. The method of claim 3, wherein the A$_3$AR agonist is selected from the group consisting of N$^6$-2-(4-aminophenyl)ethyladenosine (APNEA), N$^6$-(4-amino-3-iodobenzyl)adenosine-5'-(N-methyluronamide) (AB-MECA), N$^6$-(3-iodobenzyl)-adenosine-5'-N-methyluronamide (IB-MECA) and 2-chloro-N$^6$-(3-iodobenzyl)-adenosine-5'-N-methyluronamide (Cl-IB-MECA).

11. The method of claim 9, wherein the A$_3$AR agonist is IB-MECA.

12. The method of claim 10, wherein the A$_3$AR agonist is IB-MECA.

13. A method for reducing intraocular pressure (IOP) comprising administering to a subject having elevated IOP an amount of IB-MECA, the amount being effective to reduce IOP.

* * * * *